US008665432B2

(12) United States Patent
Hu et al.

(10) Patent No.: US 8,665,432 B2
(45) Date of Patent: Mar. 4, 2014

(54) APPARATUS FOR PERFORMING SERS (75) Inventors: Min Hu, Sunnyvale, CA (US); Michael Josef Stuke, Palo Alto, CA (US); Zhiyong Li, Redwood City, CA (US); Wei Wu, Palo Alto, CA (US); Fung Suong Ou, Palo Alto, CA (US); Shih-Yuan Wang, Palo Alto, CA (US); Lars Helge Thylen, Huddinge (SE)

(73) Assignee: Hewlett-Packard Development Company, L.P., Houston, TX (US)

( * ) Notice: Subject to any disclaimer, the term of this patent is extended or adjusted under 35 U.S.C. 154(b) by 402 days.

(21) Appl. No.: 12/915,148

(22) Filed: Oct. 29, 2010

(65) Prior Publication Data
US 2012/0105841 A1 May 3, 2012

(51) Int. Cl.
*G01N 21/65* (2006.01)
(52) U.S. Cl.
USPC .......................................... 356/301
(58) Field of Classification Search
USPC .......................................... 356/301
See application file for complete search history.

(56) References Cited

U.S. PATENT DOCUMENTS

| 5,400,136 | A  | * | 3/1995 | Vo-Dinh | 356/301 |
| 7,267,948 | B2 |   | 9/2007 | Vo-Dinh | |
| 7,738,096 | B2 |   | 6/2010 | Zhao et al. | |
| 2001/0033808 | A1 | * | 10/2001 | Wardlaw | 422/58 |
| 2010/0110424 | A1 |   | 5/2010 | Wang et al. | |

OTHER PUBLICATIONS

Liu et al. ("Nanowell surface enhanced Raman scattering arrays fabricated by soft-lithography for label-free biomolecular detections in integrated microfluidics"); Applied Physics Letters 87; 2005.*
Wackerly, Jay, "Conjugated Polymers as Fluorescence-Based Chemical Sensors", < http://www.chemistry.illinois.edu/research/organic/seminar_extracts/2004_2005/06_Wackerly_Abstract.pdf > Nov. 1, 2004, pp. 41-48.

* cited by examiner

*Primary Examiner* — Kara E. Geisel
*Assistant Examiner* — Rufus Phillips (57) ABSTRACT

An apparatus for performing surface enhanced Raman spectroscopy (SERS) includes a substrate and a plurality of nano-pillars, each of the plurality of nano-pillars having a first end attached to the substrate, a second end located distally from the substrate, and a body portion extending between the first end and the second end, in which the plurality of nano-pillars are arranged in an array on the substrate, and in which each of the plurality of nano-pillars is formed of a polymer material that is functionalized to expand in the presence of a fluid to cause gaps between the plurality of nano-pillars to shrink when the fluid is supplied onto the nano-pillars.

20 Claims, 5 Drawing Sheets

APPARATUS FOR PERFORMING SERS

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman-scattering.

Raman-scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

Unfortunately, the Raman signal produced by Raman-scattering is extremely weak in many instances compared to elastic or Rayleigh scattering from an analyte species. The Raman signal level or strength may be significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to examples thereof. In the following description, numerous specific details are set forth in order to provide a thorough understanding of the present disclosure. It will be readily apparent however, that the present disclosure may be practiced without limitation to these specific details. In other instances, some methods and structures are not described in detail so as not to unnecessarily obscure the description of the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on.

Disclosed herein are an apparatus, a system, and a method for performing surface enhanced Raman spectroscopy (SERS) to detect at least one molecule in an analyte sample with a relatively high level of precision. In one regard, the accuracy of the molecule detection is relatively high because the apparatus disclosed herein significantly increases the probability that the at least one molecule will be located near or on at least one Raman-active nano-particle to enhance Raman light emission from the at least one molecule.

As discussed in greater detail herein below, the apparatus for performing SERS includes a plurality of expandable nano-pillars that are to swell through absorption of a fluid. The swelling of the expandable nano-pillars causes gaps between the nano-pillars to shrink, thereby substantially trapping molecules in the gaps and within relatively close vicinities of the Raman active-nanoparticles. The gaps, therefore, operate as hot spots of Raman signal production from the trapped molecules. Through implementation of the apparatus, system, and method disclosed herein, the likelihood of detecting a molecule through SERS is significantly increased.

As also discussed herein below, by functionalizing the nano-pillars to react to certain materials and by detecting the intensities of Raman scattered light emitted by at least one indicator molecule, the apparatus for performing SERS may be utilized as a sensor to detect for the presence of the certain materials. In at least one example, the apparatus may be utilized to determine the amount of the one or more materials present.

Figure 1A:
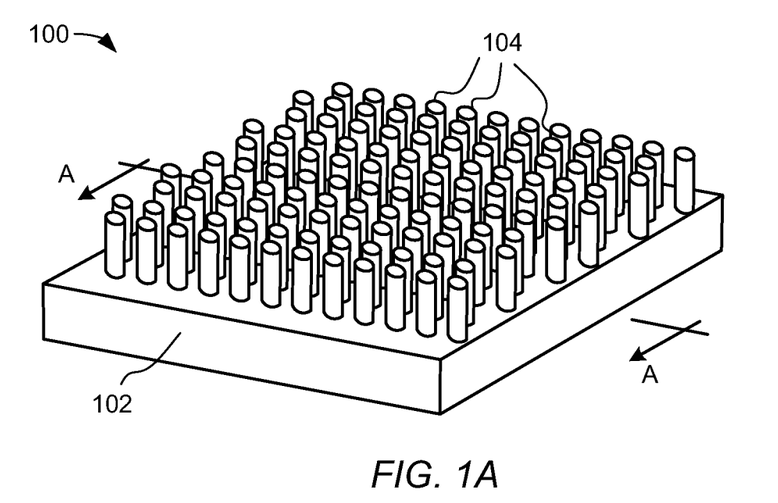
FIG. 1A shows an isometric view of an apparatus for performing SERS, according to an example of the present disclosure.

FIG. 1A shows an isometric view of an apparatus 100 for performing SERS configured in accordance with examples of the present disclosure. It should be understood that the apparatus 100 depicted in FIG. 1A may include additional components and that some of the components described herein may be removed and/or modified without departing from a scope of the apparatus 100. It should also be understood that the components depicted in FIG. 1 are not drawn to scale and thus, the components may have different relative sizes with respect to each other than as shown therein.

The apparatus 100 includes a substrate 102 and a plurality of nano-pillars 104. The substrate 102 provides a support on which the distances between the first ends or bases of the nano-pillars 104 may substantially be maintained. According to an example, the substrate 102 is composed of an insulating material or a dielectric material, including a polymer, glass, $SiO_2$, $Al_2O_3$, or any other suitable material upon which the nano-pillars 104 may be supported.

The nano-pillars 104 are depicted as being attached to and extending above a surface of the substrate 102. The nano-pillars 104 may be integrally formed with the substrate 102 or may be separately formed from the substrate 102. Thus, the nano-pillars 104 may be formed of the same material or materials as the substrate 102 or may be formed of at least one different material from the substrate 102. According to at least one example, the nano-pillars 104 are formed of a polymer material that is functionalized to expand in the presence or through absorption of at least one fluid. Suitable polymer materials for the nano-pillars 104 comprise but not limited to, for instance, polydimethylsiloxane (PDMS) elastomer, cross-linked polysilane, polyacrylate/polyacrylamide copolymers, ethylene maleic anhydride copolymer, cross-linked carboxymethylcellulose, polyvinyl alcohol copolymers, cross-linked polyethylene oxide, starch grafted copolymer of polyacrylonitrile, polystyrene copolymer, and any mixture of those polymers, etc. In various examples, the nano-pillars 104 may be fabricated through a nanoimprinting process or embossing process in which a template of relatively rigid pillars is employed in a multi-step imprinting process or embossing on a polymer matrix to form the nano-pillars 104. Various other processes, such as, but not limited to, etching, and various techniques used in the fabrication of micro-electromechanical systems (MEMS) and nano-electromechanical systems (NEMS) may also be used to fabricate the nano-pillars 104.

A nano-pillar 104 may be defined as an elongated, nanoscale structure having a length (or height) that exceeds by more than several times a nanoscale cross sectional dimension (for instance, width) taken in a plane perpendicular to the length (for instance, length>10×width). In general, the length is much greater than the width or cross sectional dimension to enable a relatively large number of nano-pillars 104 to be provided a substrate 102. In some examples, the length exceeds the cross sectional dimension (or width) by more than a factor of about 5 or 10. For example, the width may be about 100 nanometers (nm) and the height may be about 500 nm. In another example, the width at the base of the nano-pillar 104 may range between about 20 nm and about 200 nm and the length may be more than about 0.5 micrometer (μm). In other examples, the nano-pillar 104 is sized based upon the types of materials used to form the nano-pillar 104.

As shown in FIG. 1A, the nano-pillars 104 are arranged in an array on the substrate 102. In addition, the nano-pillars 104 may be randomly distributed or the nano-pillars 104 may be arranged in a predetermined configuration to therefore cause the nano-pillars 104 to be distributed in a substantially uniform density on the substrate 102. In any regard, and as discussed in greater detail herein below, the nano-pillars 104 are arranged with respect to each other such that prior to expansion, each of the nano-pillars 104 is arranged a sufficient distance apart from neighboring ones of the nano-pillars 104 to enable the at least the one fluid to be introduced into the gaps between the nano-pillars 104 and, subsequent to expansion, the gap between at least two of the nano-pillars 104 becomes sufficiently small to amplify emission of Raman signal from a molecule trapped between the at least two of the nano-pillars 104. More particularly, for instance, the nano-pillars 104 may be positioned with respect to each other such that, following expansion, the gap between at least two of the nano-pillars 104 is sufficiently small to enable a separation of less than around 5 nm. The initial arrangement of the nano-pillars 104 on the substrate 102 may thus be based upon the functionalization of the nano-pillars 104, for instance, the amount of expansion that the nano-pillars 104 are expected to experience.

The nano-pillars 104 have been depicted in FIG. 1A as having substantially cylindrical cross-sections. It should, however, be understood that the nano-pillars 104 may have other shaped cross-sections, such as, but not limited to, for instance, rectangular, square, triangular, etc. In addition, or alternatively, the tops or second ends of the nano-pillars 104 may have other shapes, such as, rounded, pyramidal, cone-shaped, etc.

Figure 1B:
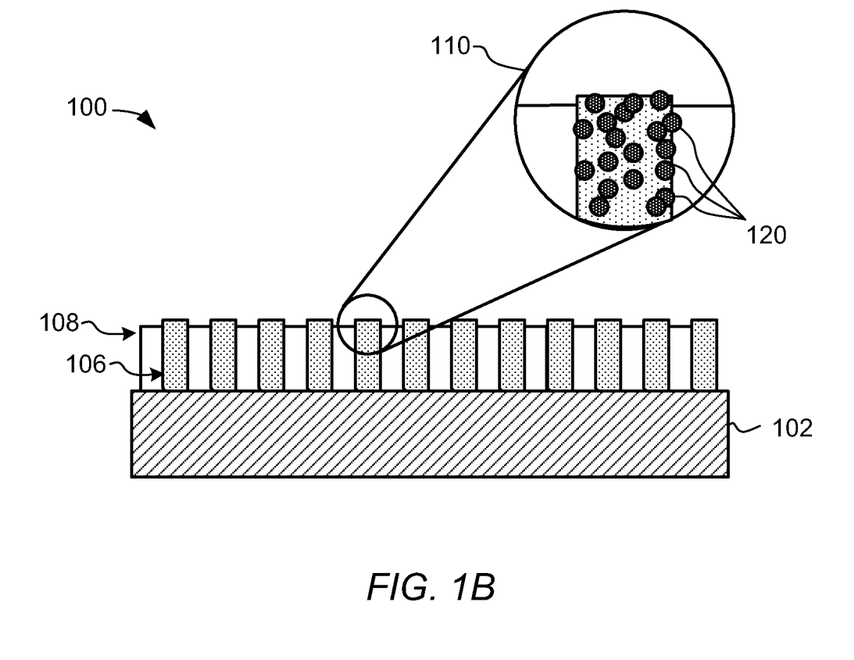
FIGS. 1B-1D, respectively, show cross-sectional views along a line A-A, shown in FIG. 1A of the apparatus, according to examples of the present disclosure.

Turning now to FIG. 1B, there is shown a cross-sectional view along a line A-A, shown in FIG. 1A, of the apparatus 100, in accordance with an example. As shown in FIG. 1B, the nano-pillars 104 positioned along one row 108 are staggered with respect to the nano-pillars 104 positioned along an adjacent row 110. In this regard, gaps between adjacent nano-pillars 104 may be bounded on two or more sides by the nano-pillars 104 located in adjacent rows 108 and 110. In addition, an end of a nano-pillar 104 is magnified in an enlargement 112, which reveals that the nano-pillar 104 includes a plurality of SERS-active nano-particles 120 disposed on the outer surface, near the tip or free end, of the nano-pillar 104. It should be understood that the enlargement 112 of the nano-pillar 104 is representative of the other nano-pillars 104.

As shown in the enlargement 110 in FIG. 1B, the SERS-active nano-particles 120 are spaced apart from each other, for instance, to enable fluid to penetrate into the underlying nano-pillars 104 and to accommodate for expansion of the nano-pillars 104 following absorption of the fluid. It should be understood that examples of the apparatus 100 are not limited to nano-particles 120 disposed over just the tips of the nano-pillars 104. In other examples, the nano-particles 120 may be disposed over part of or nearly the entire surface of the nano-pillars 104. In any regard, the SERs-active nano-particles 120 may be deposited onto at least the free ends of the nano-pillars 104 through, for instance, physical vapor deposition (PVD), chemical vapor deposition (CVD), sputtering, etc., of metallic material, or self-assembly of pre-synthesized nano-particles. By way of example, the angles at which the nano-particles 120 are deposited onto the nano-pillars 104 may be controlled to thereby substantially control the deposition of the nano-particles 120.

In addition, the nano-particles 120 may one or both of enhance Raman scattering and facilitate analyte adsorption. For instance, the nano-particles 120 may comprise a SERS or Raman-active material such as, but not limited to, gold (Au), silver (Ag), and copper (Cu) having nanoscale surface roughness. Nanoscale surface roughness is generally characterized by nanoscale surface features on the surface of the layer(s) and may be produced spontaneously during deposition of the SERS-active nano-particles 120. By definition herein, a Raman-active material is a material that facilitates Raman scattering and the production or emission of the Raman signal from an analyte adsorbed on or in a surface layer or the material during Raman spectroscopy.

In some examples, the nano-particles 120 may be annealed or otherwise treated to increase nanoscale surface roughness of the active nano-particles 120 after deposition. Increasing the surface roughness may enhance Raman scattering from an adsorbed analyte, for example. Alternatively, the arrangement of the nano-particles 120 may provide a nanoscale roughness that enhances Raman scattering, for example.

In some examples, a surface of the nano-pillars 104 may be functionalized to facilitate adsorption of the analyte. For example, the tips or free ends of the nano-pillars 104 in a vicinity thereof (not illustrated) may be functionalized with a binding group to facilitate binding with a specific target analyte species. A surface of the nano-particles 120 may be functionalized, for example. The functionalized surface of the nano-particles 120 may provide a surface to which a particular class of analytes is attracted and may bond or be preferentially adsorbed. The functionalized surface may selectively bond with protein, DNA or RNA, for example.

Figure 1C:
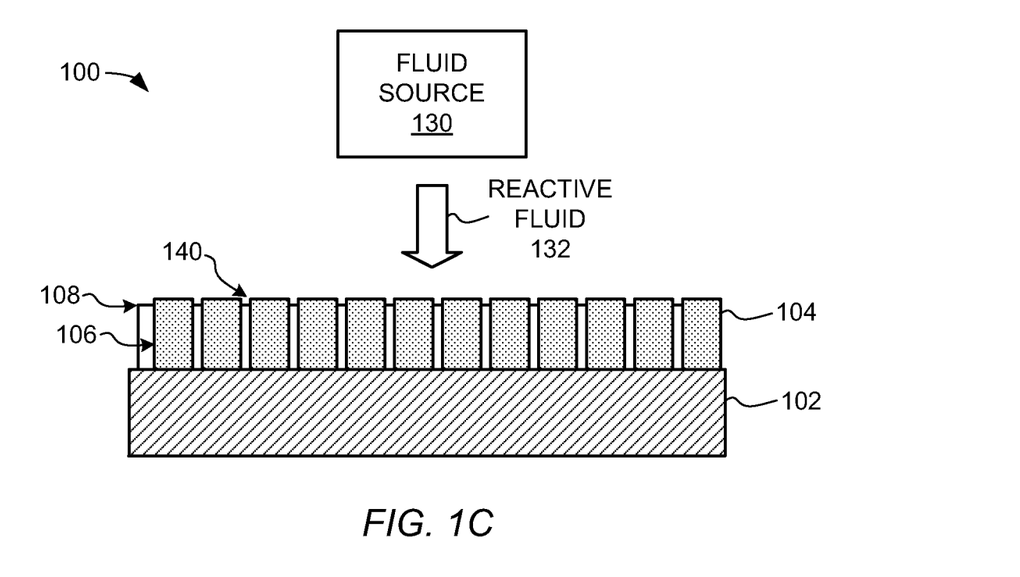

Turning now to FIG. 1C, there is shown a cross-sectional view of the apparatus 100 depicted in FIG. 1B following introduction of a reactive fluid 132, in which the nano-pillars 104 have been functionalized to react to the fluid 132, in accordance with an example of the present disclosure. As shown in FIG. 1C, the reactive fluid 132 is supplied onto the nano-pillars 106 by a fluid source 130, which may comprise, for instance, a micro-fluidic channel and reservoir. The nano-pillars 104 react to the reactive fluid 132 by swelling in size and thereby decreasing the widths of the gaps 140 between two or more of the nano-pillars 104. In the example depicted in FIG. 1C, the nano-pillars 104 are depicted as expanding substantially uniformly from top to bottom. However, in instances where the nano-pillars 104 are integrally formed or are otherwise immovably attached to the substrate 102, the bases or first ends of the nano-pillars 104 may not expand or may expand by a relatively lower amount as compared with the rest of the nano-pillars 104. An example of this type of nano-pillar 104 expansion is depicted in FIG. 1D, which shows an enlarged portion of some of the nano-pillars 104 depicted in FIG. 1B.

Figure 1D:
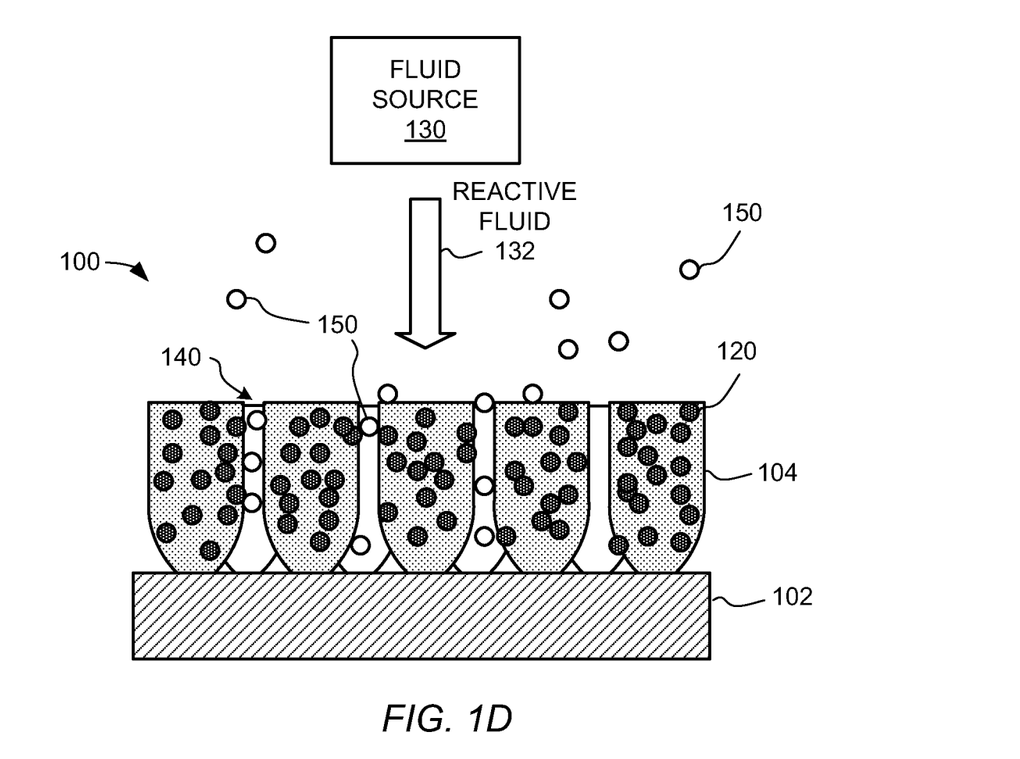

Also shown in FIG. 1D are a plurality of analyte molecules 150 that may be introduced onto the apparatus 100 in a fluid (liquid and/or gas). In one example, the analyte molecules 150 are contained in the reactive fluid 132 that is introduced onto the nano-pillars 104 by the fluid source 130 to cause the nano-pillars 104 to expand. In another example, the analyte molecules 150 are introduced in a fluid separate from the reactive fluid 132. In any regard, some of the analyte molecules 150 are depicted as being trapped in the gaps 140 between adjacent nano-pillars 104. In one regard, therefore, some of the analyte molecules 150 may be held in relatively close proximity to some of the nano-particles 120 following expansion of the nano-pillars 104. Other ones of the analyte molecules 150 have been depicted as being attached to the nano-particles 120. As such, some of the analyte molecules 150 may be adsorbed by the nano-particles 120.

The trapping of the analyte molecules 150 between some of the adjacent nano-pillars 104 may enhance a signal strength of a Raman signal produced by Raman scattering from the analyte molecules 150 due to their close proximity to the nano-particles 120. The trapping of the analyte molecules 150 also increases the likelihood that Raman light scattering from the analyte molecules 150 will be enhanced by the nano-particles 120.

Although the nano-pillars 104 have been depicted in FIGS. 1A-1D as each extending vertically and at the same heights with respect to each other, it should be understood that some or all of the nano-pillars 104 may extend at various angles and heights with respect to each other. The differences in angles and/or heights between the nano-pillars 104 may be based upon, for instance, differences arising from the fabrication of the nano-pillars 104, differences arising from the deposition of the nano-particles 120 on the nano-pillars 104, etc.

Figure 2:
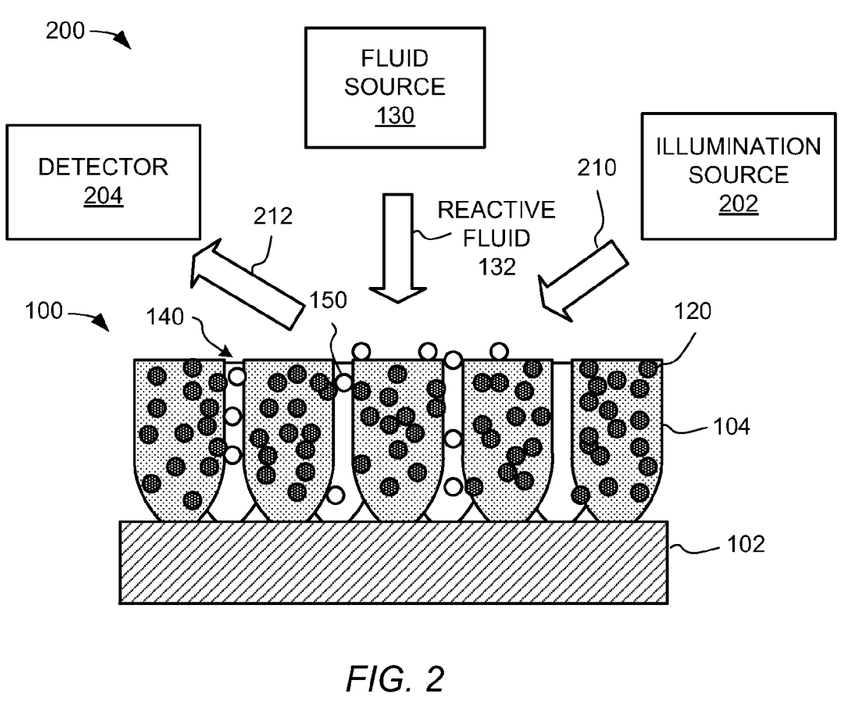
FIG. 2 shows a block diagram of a SERS system employing the apparatus depicted in FIGS. 1A-1D, according to an example of the present disclosure.

With reference now to FIG. 2, there is shown a block diagram of a surface enhanced Raman spectroscopy (SERS) system 200, according to an example. It should be understood that the system 200 depicted in FIG. 2 may include additional components and that some of the components described herein may be removed and/or modified without departing from a scope of the system 200. It should also be understood that the components depicted in FIG. 2 are not drawn to scale and thus, the components may have different relative sizes with respect to each other than as shown therein.

As shown in FIG. 2, the SERS system 200 includes the apparatus 100 depicted in FIGS. 1A-1D, an illumination source 202 and a detector 204. The fluid source 130 and the reactive fluid 132 are also depicted in FIG. 2. The apparatus 100 is further depicted as including the nano-particles 120 disposed on the nano-pillars 104, which are attached to substrate 102.

The illumination source 202 is to emit an electromagnetic radiation, such as, but not limited to, visible light, onto the nano-pillars 104, as represented by the arrow 210. By way of example, the illumination source 202 may comprise a laser that illuminates the nano-pillars 104 with visible light. The electromagnetic radiation is intended to cause the analyte molecules 150 to produce Raman scattered light as represented by the arrow 212. In addition, the detector 204 is positioned and to detect the Raman scattered light emitting from the analyte molecule(s) 150.

As discussed above, the nano-particles 120 located near or adjacent to the analyte molecule(s) 150 may enhance the production of Raman scattered light from the analyte molecule(s) 150 by concentrating or otherwise enhancing an electromagnetic field in a vicinity of the analyte molecule(s) 150. In this regard, the gaps 140 form hot spots in which production of the Raman scattered light 212 from the analyte molecule(s) 150 is substantially enhanced. In addition, the trapping of the analyte molecule(s) 150 in the gaps 140 may substantially increase the likelihood that the analyte molecule(s) 150 will be positioned near or in contact with some nano-particles 120. In this regard, the likelihood that an analyte molecule(s) 150 will produce relatively strong Raman scattered light will thus also be increased. Thus, through implementation of the system 200, the detector 204 may receive a relatively stronger Raman scattered light signal 212 from the illuminated analyte molecule(s) 150 as compared with conventional SERS systems.

The detector 204 is to convert the Raman scattered light 212 emitted from the analyte molecule(s) 150 into electrical signals that may be processed to identify, for instance, the analyte. In some examples, the detector 204 is to output the electrical signals to other components (not shown) to process the electrical signals. In other examples, the detector 204 is equipped with processing capabilities to identify the analyte.

According to at least one example, the SERS system 200 may be employed as a sensor to determine whether at least one analyte is present in a fluid supplied to the nano-pillars 104. In this at least one example, the molecules 140 comprise indicator molecules 150 attached to the nano-pillars 104 prior to expansion of the nano-pillars 104. The SERS system 200 may be implemented to detect the Raman signal emitted from the indicator molecules 150 to determine an approximate Raman signal signature of the indicator molecules 150. In addition, the nano-pillars 104 may be functionalized to expand through absorption of at least one analyte. When the at least one analyte is introduced onto and absorbed by the nano-pillars 104, the nano-pillars 104 are to expand, thereby causing the gaps 140 to decrease, which may result in an increase in the Raman signals emitted by the Raman tagged molecules. In this regard, when the detector 204 determines that the detected Raman signals have increased, a determination that the at least one particular analyte is present may be made. In addition, the amount of the analyte that caused the nano-pillars 104 to expand may also be determined based upon the relative strength of the detected Raman signals.

By way of particular example in which the analyte is water or other fluid, the SERS system 200 may be employed to determine the level of humidity present in the air surrounding the apparatus 100. In this example, as the humidity level rises, the nano-pillars 104 are to absorb greater amounts of water molecules and therefore continually expand. As the nano-pillars 104 continually expand, the Raman signals emitted by the Raman tagged molecules will also likely increase. The humidity may therefore be determined based upon the strength of the detected Raman signals emitted by the Raman tagged molecules.

As another example, different ones of the nano-pillars 104 may be functionalized to expand through absorption of different analytes. Thus, for instance, a first set of nano-pillars 104 located in one section of the substrate 102 may be formed of a first polymer material that is functionalized to expand through absorption of a first type of fluid ad a second set of nano-pillars 104 located in another section of the substrate 102 may be formed of a second polymer material that is functionalized to expand through absorption of a second type of fluid. In this example, the location on the substrate 102 where increases in the Raman signal are detected may be analyzed to determine which type of fluid or fluids are present to have caused the increase in the Raman signal. Thus, for instance, in an apparatus 100 composed of a matrix of nano-pillars 104 formed of polymer materials that have been functionalized to react with different types of materials, the particular type of analyte may be determined through a determination of which of the nano-pillars 104 have expanded.

Figure 3:
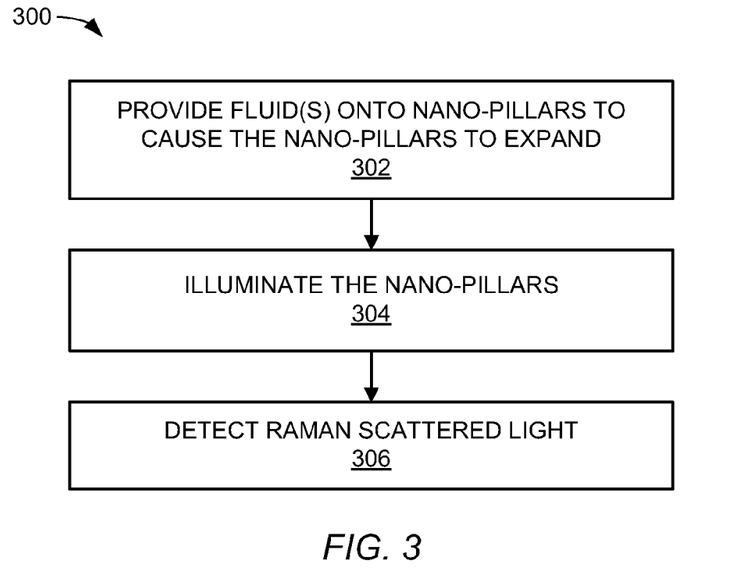
FIGS. 3 and 4, respectively, show flow diagrams of methods 300 and 400 for performing SERS on the apparatus depicted in FIGS. 1A-1D implementing the SERS system depicted in FIG. 2, according to an example of the present disclosure.
Figure 4:
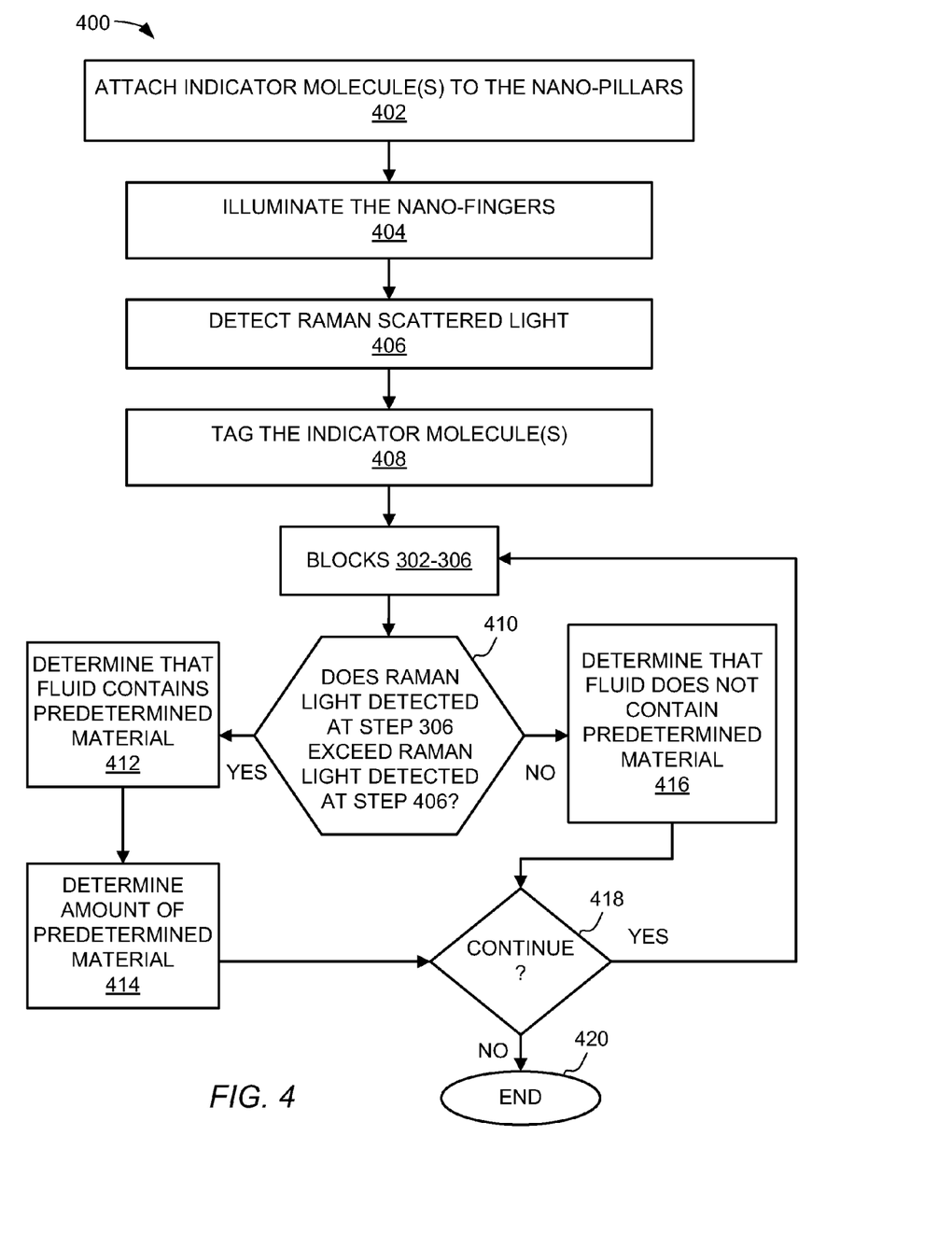

Various manners in which the SERS system 200 may be employed to perform SERS on the apparatus 100 are depicted in FIGS. 3 and 4. FIGS. 3 and 4, more particularly, depict respective flow diagrams of methods 300 and 400 for performing SERS on the apparatus 100, according to examples of the disclosure. It should be understood that the methods 300 and 400 may include additional operations and that some of the operations described therein may be removed and/or modified without departing from scopes of the methods 300 and 400. In addition, FIG. 3 generally depicts a method 300 for performing SERS on the apparatus 100 to identify an analyte molecule 150 and FIG. 4 generally depicts a method 400 for determining whether at least one particular analyte is likely present in a fluid sample supplied on the apparatus 100. In this regard, the method 400 may be implemented to sense or detect when a particular analyte is likely present in the fluid sample or to determine the likely composition of the fluid sample.

With reference first to FIG. 3, at block 302, the nano-pillars 104 are provided with a reactive fluid 132 from the fluid source 130 to cause the nano-pillars 104 to expand, which results in the gaps 140 between the nano-pillars 104 to shrink. The shrinking of the gaps 140 causes analyte molecules 150, which may have been provided in the reactive fluid 132 or in another fluid, to become trapped between adjacent ones of the nano-pillars 104.

At block 304, the illuminating source 202 is activated to illuminate the nano-pillars 104. As discussed above, the trapping of the analyte molecules 150 and the nano-particles 120 are to enhance the probability of and the production of Raman scattered light emitted from the analyte molecules 202.

At block 306, the detector 204 detects the Raman scattered light 212, if any, produced from the analyte molecule(s) 150. As discussed above, the detected Raman scattered light may be processed to identify the analyte. In another example, however, and as shown in FIG. 4, the detected Raman scattered light may be processed to determine whether the analyte is present in a fluid supplied to the nano-pillars 104.

More particularly, with reference to FIG. 4, at block 402, at least one indicator molecule, which may comprise the analyte molecules 150, are attached to the nano-pillars 104. The indicator molecule(s) may comprise any suitable molecule that does not substantially react with the nano-pillars 104 and therefore does not cause the nano-pillars 104 to substantially expand. As such, for instance, the indicator molecule(s) may be introduced onto the nano-pillars 104 in a fluid to which the nano-pillars 104 have not been functionalized to absorb.

At block 404, the illuminating source 202 is activated to illuminate the nano-pillars 104. Thus, at block 404, the nano-pillars 104, including the indicator molecule(s) 150 are illuminated prior to expansion of the nano-pillars 104.

At block 406, the detector 204 detects the Raman scattered light 212, if any, produced from the indicator molecule(s) 150. In addition, at block 408, the indicator molecule(s) 150 may be tagged based upon the intensity of the Raman scattered light 212 produced by the indicator molecule(s) 150. In an example in which a single type of polymer material is employed in the nano-pillars 104, the intensity of the Raman light emission by at least one indicator molecule 150 may be identified and stored at block 408. In an example in which multiple types of polymer materials functionalized to expand upon absorption of different types of analytes, are employed in the nano-pillars 104, the intensities of the Raman light emissions by indicator molecules 150 attached to the different types of nano-pillars 104 may be identified and stored at block 408.

Following the tagging of the indicator molecule(s) 150 at block 408, blocks 302-306 may be performed to detect the Raman scattered light from the indicator molecule(s) 150. In addition, at block 410, a determination as to whether the intensity of the Raman scattered light detected at block 306 exceeds the intensity of the Raman scattered light detected at block 406 is made. The intensity of the Raman scattered light is likely to increase when the nano-pillars 104 have expanded and thus, when the intensity of the Raman scattered light detected at block 306 is determined to exceed the intensity of the Raman scattered light detected at block 406, the fluid supplied at block 302 is determined as containing a predetermined material. The predetermined material comprises a material with which the polymer material of the nano-pillars 104 has been functionalized to react, for instance, by expanding through absorption of the predetermined material.

At block 414, the amount of the predetermined material may optionally be determined, for instance, based upon the difference in intensities of the Raman scattered light detected at blocks 306 and 406. The intensity difference may be used to determine the amount of the predetermined material contained in the fluid because that amount may directly affect the amount of expansion that occurs in the nano-pillars 104 and thus, the effect that the nano-particles 120 have in the production of the Raman scattered light by the indicator molecule(s) 150. Following determination that the fluid contains a predetermined material and/or the amount of the predetermined material, this information may be outputted or may be stored.

With reference back to block 410, if the intensity of the Raman scattered light detected at block 306 does not exceed the intensity of the Raman scattered light detected at block 406, the fluid supplied at block 302 is determined as not containing the predetermined material. In other words, since the fluid supplied at block 302 does not likely contain a material to cause the nano-pillars 104 to expand, the effect that the nano-particles 120 have on the indicator molecule(s) 150 is not likely to vary between blocks 306 and 406.

Following either or both of blocks 414 and 415, a decision as to whether the method 400 is to continue may be made as indicated at block 418. The method 400 may continue at block 418 to continue to track for particular at least one predetermined material. Otherwise, the method 400 may end as indicated at block 420.

Although not explicitly depicted in FIG. 4, the method 400 may be implemented on a plurality of nano-pillars 104, in which different sets of the plurality of nano-pillars 104 have been functionalized to react with different types of materials. As such, the same apparatus 100 may be employed to detect different types of materials, as well as the composition of analytes.

Figure 5:
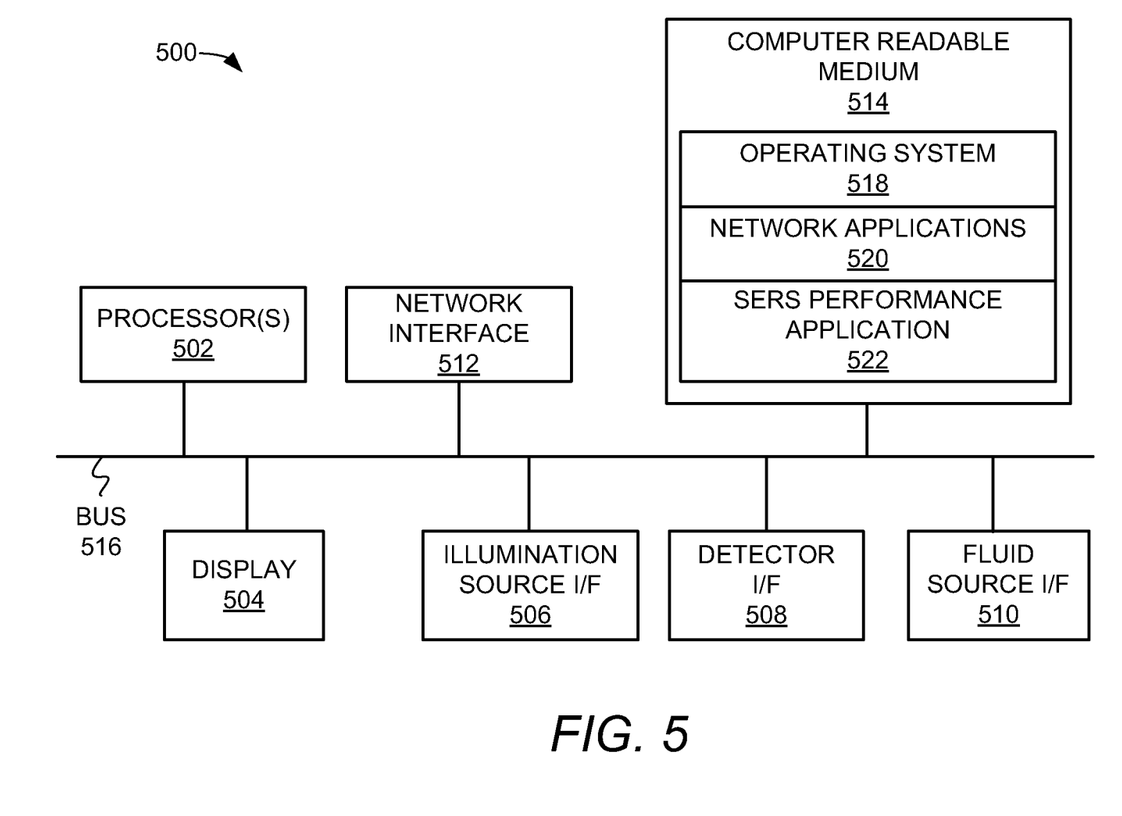
FIG. 5 shows a schematic representation of a computing device configured to implement one or both of the methods depicted in FIGS. 3 and 4, according to an example of the present disclosure.

Turning now to FIG. 5, there is shown a schematic representation of a computing device 500 to implement or execute one or both of the methods 300 and 400, in accordance with examples of the present disclosure. The computing device 500 may comprise, for instance, a desktop computer, laptop, server, etc. The computing device 500 includes at least one processor 502, such as, but not limited to, a central processing unit; at least one display device 504, such as a monitor; an illumination source interface (I/F) 506; a detector interface 508; a fluid source interface 510; at least one network interface 512, such as a Local Area Network LAN, a wireless 802.11x LAN, a 3G mobile WAN or a WiMax WAN; and at least one computer-readable medium 514. Each of these components is operatively coupled to at least one bus 516. For example, the bus 516 may be an EISA, a PCI, a USB, a FireWire, a NuBus, or a PDS.

The computer readable medium 514 may be any suitable medium that participates in providing instructions to the processor 502 for execution. For example, the computer readable medium 510 may be non-volatile media, such as, but not limited to, an optical or a magnetic disk; volatile media, such as memory; and transmission media, such as coaxial cables, copper wire, and fiber optics. Transmission media can also take the form of acoustic, light, or radio frequency waves.

The computer-readable medium 510 may also store an operating system 518, such as, but not limited to, Mac OS, MS Windows, Unix, or Linux; network applications 520; and a SERS performance application 522. The operating system 518 may be multi-user, multiprocessing, multitasking, multithreading, real-time and the like. The operating system 518 may also perform basic tasks such as, but not limited to, recognizing input from input devices, such as a keyboard or a keypad; sending output to the display 504, the illuminating source 302, the detector 304, and the fluid source 120; keeping track of files and directories on medium 514; controlling peripheral devices, such as disk drives, printers, image capture device; and managing traffic on the at least one bus 516. The network applications 520 include various components for establishing and maintaining network connections, such as machine readable instructions for implementing communication protocols including TCP/IP, HTTP, Ethernet, USB, and FireWire.

The SERS performance application 522 provides various machine readable instructions components for performing SERS on an apparatus, as described above. In certain examples, some or all of the processes performed by the SERS performance application 522 may be integrated into the operating system 518. In certain examples, the processes can be at least partially implemented in digital electronic circuitry, or in computer hardware, machine readable instructions (including firmware and/or software), or in any combination thereof.

What has been described and illustrated herein are various examples of the disclosure along with some of their variations. The terms, descriptions and figures used herein are set forth by way of illustration only and are not meant as limitations. Those skilled in the art will recognize that many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing surface enhanced Raman spectroscopy (SERS), said apparatus comprising:
    a substrate; and
    a plurality of nano-pillars, each of the plurality of nano-pillars having a first end attached to the substrate, a second end located distally from the substrate, and a body portion extending between the first end and the second end, wherein the body portion has a length extending from the first end to the second end that is greater than a width of the body portion, wherein the plurality of nano-pillars are arranged in an array on the substrate, and wherein each of the plurality of nano-pillars is formed of a polymer material that is functionalized to expand in the presence of a fluid to cause gaps between the plurality of nano-pillars to shrink when the fluid is supplied onto the nano-pillars.

2. The apparatus according to claim 1, wherein, prior to expansion, each of the plurality of nano-pillars is arranged a sufficient distance apart from neighboring ones of the plurality of nano-pillars to enable the fluid to be introduced into the gaps between the plurality of nano-pillars and, subsequent to expansion, the gap between a plurality of the plurality of nano-pillars becomes sufficiently small to amplify emission of Raman signal from a molecule trapped between the plurality of nano-pillars.

3. The apparatus according to claim 1, further comprising:
    SERS-active nano-particles disposed on the plurality of nano-pillars, wherein the SERS-active nano-particles are to enhance Raman light emission from a molecule that is on or sufficiently close to the SERS-active nano-particles.

4. The apparatus according to claim 3, wherein the SERS-active nano-particles are disposed at least on top of the second ends of the plurality of nano-pillars.

5. The apparatus according to claim 3, wherein the SERS-active nano-particles are disposed along a side wall of the plurality of nano-pillars.

6. The apparatus according to claim 1, further comprising:
    an indicator molecule attached to at least one of the plurality of nano-pillars, wherein the indicator molecule is to emit a first Raman signal prior to expansion of the polymer material and to emit a second Raman signal following expansion of the polymer material, wherein the second Raman signal is relatively stronger than the first Raman signal.

7. The apparatus according to claim 1, further comprising:
    a first set of nano-pillars formed of a first polymer material functionalized to expand in the presence of a first type of fluid;
    a second set of nano-pillars formed of a second polymer material functionalized to expand in the presence of a second type of fluid; and
    a plurality of indicator molecules positioned on the first set of nano-pillars and the second set of nano-pillars, and wherein the first set of nano-pillars and the second set of nano-pillars are arranged on separate sections of the substrate.

8. The apparatus according to claim 1, wherein the polymer material comprises a polymer selected from the group consisting of polydimethylsiloxane (PDMS) elastomer, cross-linked polysilane, polyacrylate/polyacrylamide copolymers, ethylene maleic anhydride copolymer, cross-linked carboxymethylcellulose, polyvinyl alcohol copolymers, cross-linked polyethylene oxide, starch grafted copolymer of polyacrylonitrile, polystyrene copolymer, and a combination thereof.

9. A surface enhanced Raman spectroscopy (SERS) system comprising
  an apparatus for performing SERS, said apparatus comprising:
    a substrate; and
    a plurality of nano-pillars, each of the plurality of nano-pillars having a first end attached to the substrate, a second end located distally from the substrate, and a body portion extending between the first end and the second end, wherein the body portion has a length extending from the first end to the second that is greater than a width of the body portion, wherein the plurality of nano-pillars is arranged in an array on the substrate, and wherein each of the plurality of nano-pillars is formed of a polymer material that is functionalized to expand in the presence of a fluid to causes gaps between the plurality of nano-pillars to shrink when the fluid is supplied onto the nano-pillars;
  an illumination source to illuminate the plurality of nano-pillars to produce a Raman scattered light from a molecule positioned on and near the plurality of nano-pillars; and
  a detector positioned to detect the Raman scattered light emitting from the molecule.

10. The system according to claim 9, wherein, prior to expansion, each of the plurality of nano-pillars is arranged a sufficient distance apart from neighboring ones of the plurality of nano-pillars to enable the fluid to be introduced into the gaps between the plurality of nano-pillars and, subsequent to expansion, the gap between the plurality of nano-pillars becomes sufficiently small to amplify emission of Raman signal from a molecule trapped between the plurality of nano-pillars.

11. The system according to claim 9, further comprising:
  SERS-active nano-particles disposed on the plurality of nano-pillars, wherein the SERS-active nano-particles are to enhance Raman light emission from a molecule on or near the SERS-active nano-particles.

12. The system according to claim 9, further comprising:
  an indicator molecule attached to one of the plurality of nano-pillars, wherein the indicator molecule is to emit a first Raman signal prior to expansion of the polymer material and to emit a second Raman signal following expansion of the polymer material, wherein the second Raman signal is relatively stronger than the first Raman signal.

13. The system according to claim 12, wherein the detector is to identify that the fluid contains a particular analyte material in response to a determination that the indicator molecule emitted the second Raman signal.

14. The system according to claim 9, further comprising:
  a first set of nano-pillars formed of a first polymer material functionalized to expand in the presence of a first type of fluid;
  a second set of nano-pillars formed of a second polymer material functionalized to expand in the presence of a second type of fluid;
  a plurality of indicator molecules positioned on the first set of nano-pillars and the second set of nano-pillars, and wherein the first set of nano-pillars and the second set of nano-pillars are arranged on separate sections of the substrate; and
  wherein the plurality of indicator molecules is to emit a first Raman signal prior to expansion of the one of the first polymer material and the second polymer material and to emit a second Raman signal following expansion of the one of the first polymer material and the second polymer material, wherein the second Raman signal is relatively stronger than the first Raman signal.

15. The system according to claim 14, wherein the detector is to identify that the fluid contains a particular analyte based upon a determination of the locations on the substrate where the second Raman signal was emitted.

16. A method for performing surface enhanced Raman spectroscopy (SERS) on an apparatus having a plurality of nano-pillars having first ends attached to a substrate, second ends located distally from the substrate, and body portions extending between the first ends and the second ends, wherein the body portions have lengths extending from the first ends to the second ends that is greater than widths of the body portions, wherein the plurality of nano-pillars are arranged in an array on the substrate, and wherein each of the plurality of nano-pillars is formed of a polymer material that is functionalized to expand in the presence of at a fluid, said method comprising:
  a) providing the fluid onto the plurality of nano-pillars to cause the plurality of nano-pillars to expand thereby cause gaps between the plurality of nano-pillars to shrink, wherein the shrinking of the gaps is to trap analyte molecules between adjacent ones of the plurality of nano-pillars;
  b) illuminating the plurality of nano-pillars to produce a Raman scattered light from the analyte molecules; and
  c) detecting the Raman scattered light produced from the analyte molecules.

17. The method according to claim 16, wherein the fluid comprises the analyte molecules.

18. The method according to claim 16, further comprising: prior to a)-c),
  d) attaching an indicator molecule to one of the plurality of nano-pillars;
  e) illuminating the plurality of nano-pillars to produce a Raman scattered light from the indicator molecule;
  f) detecting the Raman scattered light from the indicator molecule; and
  g) tagging the indicator molecule with a first signal associated with the Raman scattered light detected from the indicator molecule.

19. The method according to claim 18, wherein the analyte molecules comprise the indicator molecule, said method further comprising:
  following a)-c),
  h) determining whether an intensity of the Raman scattered light detected at c) exceeds the intensity of the Raman scattered light detected at f) by at least a predetermined amount;
  i) in response to a determination that the Raman scattered light detected at c) exceeds the Raman scattered light detected at f) by at least the predetermined amount, determining that the fluid comprises a predetermined material, wherein the plurality of nano-pillars are to react with the predetermined material; and
  j) in response to a determination that the Raman scattered light detected at c) does not exceed the Raman scattered light detected at f) by at least the predetermined amount, determining that the fluid does not comprise the predetermined material.

20. The method according to claim 19, further comprising:

k) determining the difference between the Raman scattered light detected at c) and the Raman scattered light detected at f); and l) determining an amount of the predetermined material contained in the fluid based upon the difference.

* * * * *